United States Patent [19]

Stephens et al.

[11] Patent Number: 4,863,456
[45] Date of Patent: Sep. 5, 1989

[54] DOSAGE FORM WITH IMPROVED DELIVERY CAPABILITY

[75] Inventors: Sally I. Stephens, Mountain View; Patrick S. L. Wong, Hayward, both of Calif.

[73] Assignee: ALZA Corporation, Palo Alto, Calif.

[21] Appl. No.: 153,306

[22] Filed: Feb. 8, 1988

Related U.S. Application Data

[63] Continuation of Ser. No. 857,265, Apr. 30, 1986, abandoned.

[51] Int. Cl.$^4$ ............................................. A61K 4/22
[52] U.S. Cl. ................................. 604/892.1; 424/422; 424/464
[58] Field of Search ............................ 604/890–897; 424/489–494, 464, 422, 438

[56] References Cited

U.S. PATENT DOCUMENTS

| | | | |
|---|---|---|---|
| 3,732,865 | 5/1973 | Higuchi et al. | 604/892.1 |
| 3,929,132 | 12/1975 | Higuchi | 128/260 |
| 3,995,632 | 12/1976 | Nakano et al. | 128/260 |
| 4,111,201 | 9/1978 | Theeuwes | 128/260 |
| 4,111,202 | 9/1978 | Theeuwes | 128/260 |
| 4,309,996 | 1/1982 | Theeuwes | 128/260 |
| 4,327,725 | 5/1982 | Cortese et al. | 128/260 |
| 4,608,048 | 8/1986 | Cortese et al. | 604/890 |
| 4,612,008 | 9/1986 | Wong et al. | 604/892 |
| 4,612,186 | 9/1986 | Echenhoff et al. | 604/892.1 |

OTHER PUBLICATIONS

*THE MERCK INDEX*, 10th Ed., Merck & Co., Rahway, N.J., (1983), p. 308, No. 2157.

*Primary Examiner*—C. Fred Rosenbaum
*Assistant Examiner*—Mark F. Colosimo
*Attorney, Agent, or Firm*—Paul L. Sabatine; Edward L. Mandell; Steven F. Stone

[57] ABSTRACT

A dosage form is disclosed comprising a wall surrounding a compartment housing a first layer comprising a drug formulation, a middle layer comprising a hydrophobic composition, and a third layer comprising a hydrophilic composition.

5 Claims, 1 Drawing Sheet

DOSAGE FORM WITH IMPROVED DELIVERY CAPABILITY

CROSS-REFERENCE TO RELATED APPLICATION

This application is a continuation of U.S. appln. Ser. No. 06/857,265 filed Apr. 30, 1986 now abandoned which application is incorporated herein by reference and benefit is claimed of its filing date.

FIELD OF THE INVENTION

The present invention pertains to a dosage form with improved delivery capability. More particularly, the dosage form comprises a first layer comprising a drug formulation, a third layer comprising a hydrophilic composition, and a second layer comprising a hydrophobic composition interposed between the first and third layers. The second layer substantially prevents the migration of drug formulation from the first layer into the third layer with its entrapment in the third layer, thereby assuring the maximum amount of the drug formulation is available for delivery from the dosage form.

BACKGROUND OF THE INVENTION

Dosage forms for delivering a beneficial agent, mainly a beneficial drug, to environments of use are known to the prior art in U.S. Pat. No. 3,845,770 issued to Felix Theeuwes and Takeru Higuchi, and in U.S. Pat. No. 3,916,899 issued to the same patentees. The dosage forms disclosed in the patents comprises a wall that surrounds an internal compartment containing the beneficial agent. The wall is permeable to the passage of an external fluid and substantially impermeable to the passage of beneficial agent. There is at least one passageway through the wall for delivering the beneficial agent from the dosage form. These dosage forms release the agent by fluid being imbibed through the wall into the compartment at a rate determined by the permeability of the wall and the osmotic pressure gradient across the wall to produce an aqueous solution containing agent that is dispensed through the passageway from the dosage form. These dosage forms are extraordinarily effective for delivering an agent that is soluble in fluid imbibed into the dosage form and exhibits an osmotic pressure gradient across the wall against the external fluid.

A pioneer advancement in dosage forms was presented to the delivery arts by Richard Cortese and Felix Theeuwes in U.S. Pat. No. 4,327,725. The invention in this patent enhances the delivery kinetics of the dosage form, for delivering agents with various degrees of solubility in aqueous fluids that are difficult to deliver, by manufacturing the dosage form with a hydrogel. The hydrogel in presence of fluid that enters the dosage form, swells and moves from a rested state to an expanded state. The increase in volume of the hydrogel acts as a driving force that is applied against the beneficial agent thereby urging the beneficial agent through the passageway from the dosage form.

The dosage form operates successfully for its intended use, and it can delivery numerous difficult to deliver agents. Its use, however, can be limited for agents that exhibit a high degree of solubility in an aqueous medium that enters the dosage form. That is, these agents can migrate into the fluid-expanding hydrogel become entrapped therein and, consequently, they are not available for delivery from the dosage form. It will be appreciated by those versed in the delivery arts, that if a dosage form is provided comprising means for substantially preventing the migration and the entrapment of the beneficial agent, such a dosage form would have a positive practical value and it would also represent both an unobvious improvement and advancement in the dispensing arts.

OBJECTS OF THE INVENTION

Accordingly, it is an immediate object of this invention to provide a dosage form for the controlled delivery of a beneficial agent, and which dosage form represents a further improvement and advancement in the delivery arts.

Another object of this invention is to provide a novel and useful dosage form manufactured as an osmotic delivery device, the use of which dosage form requires intervention only for initiation of its use for producing a beneficial result.

Another object of this invention is to provide a dosage form that can deliver a substantial amount of a beneficial agent at a rate controlled by the dosage form throughout the day with once, and sometimes twice daily dosing by the dosage form.

Another object of the invention is to provide a dosage form having a compartment comprising a beneficial agent that is from soluble to very soluble in an aqueous fluid, an expandable hydrophilic hydrogel, and means for substantially preventing the migration of the beneficial agent into the hydrophilic hydrogel.

Another object of the invention is to provide a dosage form having a compartment containing an agent formulation that is soluble to very soluble in an aqueous fluid, an expandable driving member comprising a hydrophilic hydrogel, and a hydrophobic composition interposed between the agent formulation and the hydrophilic hydrogel, and which hydrogel operates by expanding to diminish the volume occupied by the beneficial agent, thereby delivering the agent from the dosage form at a controlled rate over time.

Another object of the invention is to provide a dosage form manufactured as an osmotic device sized and adapted for admitting into a biological environment of use for a particular time period for delivering the major amount of a beneficial agent throughout the osmotic device's agent releasing history.

Another object of the invention is to provide an osmotic device having a compartment housing a layer of a beneficial agent formulation, an adjacent layer of a hydrophobic composition in which layer the agent formulation is poorly or substantially insoluble, and an adjacent layer of an expandable driving member comprising a hydrogel, which hydrogel can continuously increase its volume while correspondingly decrease the volume initially occupied by the agent formulation with the volume occupied by the hydrophobic layer remaining substantially unchanged throughout the operation of the osmotic device.

Another object of the invention is to provide a dosage form adapted and shaped as an oral, osmotic dosage form that can continuously maintain substantially the major amount of the beneficial agent present for delivery and free from being retained in the dosage form throughout the agents release from the dosage form when in operation in the gastrointestinal tract.

Other objects features, aspects and advantages of the invention will be more apparent to those skilled in the pharmaceutical arts from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows.

In the drawings and in the specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 1:
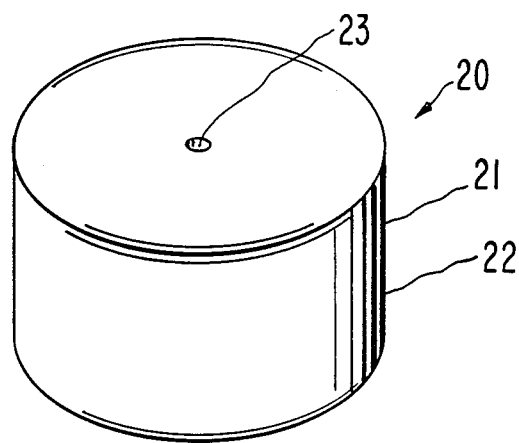
FIG. 1 is a view of a dosage form adapted, shaped and sized as an oral, osmotic device for administering a beneficial drug to the gastrointestinal tract of a warm-blooded animal over a prolonged period of time.

Turning now to the drawing figures in detail, which drawing figures are an example of the dosage form provided by the invention, and which example is not to be construed as limiting the invention one example is the dosage form, manufactured as an osmotic device, as illustrated in FIG. 1 by the numeral 20. In FIG. 1, the osmotic dosage form 20 comprises a body member 21 comprising a wall 22 that surrounds and forms an internal compartment, not seen in FIG. 1. Dosage form 20 comprises at least one exit passageway 23 for connecting the interior of dosage form 20 with the exterior environment, and more preferably a biological environment of use.

Figure 2:
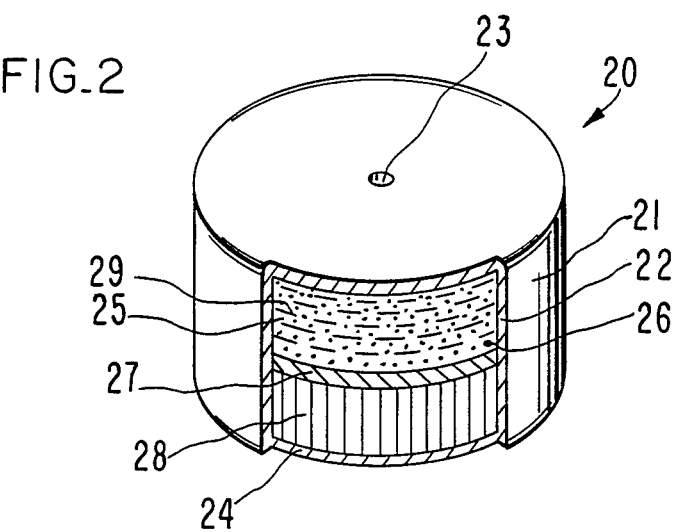
FIG. 2 is a partially opened view of the dosage form of FIG. 1 with a part of the exterior wall of the dosage form sectioned-away for illustrating the structure of the dosage form; and, FIG. 3 is a view of the opened dosage form of FIG. 2, with the dosage form in FIG. 3 depicting the internal structure of the dosage form nearing the end of the drug delivery period.

In FIG. 2, osmotic dosage form 20 is seen in opened view with wall 22 sectioned at 24. In FIG. 2, dosage form 20 comprises body 21, wall 22 that surround and defines an internal compartment 25, and at least one passageway 23 for dispensing the contents of compartment 25 from dosage form 20.

Wall 22 of dosage form 20 comprises totally, or in at least a part, a composition that is permeable to the passage of an exterior fluid present in the environment of use. Wall 22 is substantially impermeable to the passage of a beneficial agent and other optional ingredients that may be present in compartment 25. Semipermeable wall 22 is substantially inert, that is, it maintains its physical and chemical integrity during the dispensing of a beneficial agent from dosage form 20. The phrase "keeps its physical and chemical integrity" means wall 22 does not lose its structure and it does not substantially change during the dispensing life of dosage form 20. Wall 22 in a presently preferred embodiment is formed totally or in at least a part of a member selected from the group consisting of cellulose acylate, cellulose diacylate, cellulose triacylate, cellulose acetate, cellulose triacetate, and the like. The composition comprising wall 22 may additionally contain (a) hydroxypropyl cellulose or (b) hydroxypropyl cellulose and polyethylene glycol. In one presently preferred manufacture wall 22 comprises 100 wt % cellulose acylate, diacylate or triacylate. In another embodiment wall 22 comprises 70 to 80 wt % cellulose acylate, diacylate or triacylate and 20 to 30 wt % hydroxypropyl cellulose with the total amount of the wall forming members equal to 100 wt %. In another manufacture wall 22 comprises 85 to 95 wt % cellulose acylate, diacylate, or triacylate and 5 to 15 wt % polyethylene glycol, with the total amount of wall forming ingredients equal to 100 wt %. In yet another preferred manufacture, wall 22 comprises 55 to 70 wt % cellulose acylate, diacylate or triacylate, 20 to 30 wt % hydroxypropyl cellulose, and 5 to 15 wt % polyethylene glycol, with the total amount of the wall forming members equal to 100 wt %.

Internal compartment 25 of dosage form 20 house a first layer comprising a dispensable agent formulation 26, identified by dots, a middle layer in contact arrangement with the first layer, which middle layer comprises non-expandable hydrophobic composition, and a third layer 28, distant from the first layer and in contact arrangement with the middle layer, which third layer 28 comprises hydrophilic composition.

The expression beneficial agent 26, as used herein, includes any beneficial agent or compound that can be delivered from dosage form 20 to produce a beneficial and useful result. In the specification and the accompanying claims, the term agent includes drug, and the term drug includes any physiologically or pharmacologically active substance that produces a local or a systemic effect in animals, including warm-blooded mammals, humans, primates, avains, sport, farm, zoo animals and the like. Exemplary drugs that are soluble or very soluble in water and can be delivered by the dosage form include prochlorperazine, ferrous sulfate, potassium chloride, procainamide hydrochloride, amphetamine sulfate, oxprenolol hydrochloride, metoprolol tartrate, and the like.

The solubility of a drug in an aqueous liquid, such as fluid 29 imbibed through wall 22 into compartment 26 during operation of dosage form 20 can be determined by various art known techniques. One technique consists of preparing a solution of a given drug and ascertaining by analysis the amount of drug present in a definite quantity of fluid, such as an aqueous-type fluid including a biological fluid. A simple apparatus for this purpose consists of a test tube of medium size fastened upright in a bath maintained at constant temperature. The fluid and the drug are placed in the tube and stirred. After a given period of stirring, a definite weight of solution is analyzed and the stirring continued for an additional period of time. If the analysis shows no increase of dissolved drug after the second period of stirring, the results are taken as the degree of solubility of the drug in the aqueous media. Generally, on a weight basis at 25° C. the amount of drug dissolved in aqueous media that is termed soluble is about a part of drug to 5 to 25 parts of aqueous media. Details of various methods for determining solubilities are described in United States Public Health Service Bulletin No. 67 of the Hygienic Laboratory; *Encyclopedia of Science and Technology*, Vol. 12, pages 542 to 556, 1971 published by McGraw-Hill, Inc., and *Encyclopedic Dictionary of Physics*, Vol. 6, pages 545 to 557, 1962, published by Pergamon Press, Inc.

Layer 27 of dosage form 20, in laminated position with drug layer 26 and hydrophobic hydrogel layer 28, is formed of a hydrophobic composition that exhibits poor solubility to drug 26. Drug 26 is poorly soluble in layer 27 and accordingly it does not migrate into layer 27 and it is not entrapped in layer 27. Typical material that can be used for forming layer 27 include the polyolefins, polyethylene, polypropylene, polytetrafluoroethylene, polystyrene, polyvinyl formal, polyvinyl butyral, polyvinylidene chloride, polyamide, polyethylene terephthalate, polyaminotriazole, glass, and the like. The materials can be used in a sheet form and pressed laminate to layer 28, or the materials can be use in a crystalline form. In this latter form, the crystalline polymer is prepared by grinding the polymer to an average particle size of 1 to 15 microns, followed by applying and pressing a 1 to 7 mm layer against layer 28.

The rate of migration of a drug into these materials can easily be determined by those skilled in the art by standard procedures. In this manner, particular materials can be selected for forming layer 27. Various techniques, such as the transmission method, the sorption-desorption methods, and the like can be used to ascertain the rate of migration, or the rejection rate of the polymer to any preselected drug. One technique that can be used is to cast a film of the material to a thickness in the range of 2 to 20 mils, (0.05 mm to 0.512 mm), that is used as a barrier between a rapidly stirred saturated solution of a drug, for example 150 r.p.m., and a solvent-sink at a constant temperature, for example 37° C. Then, samples are periodically withdrawn from the solvent-sink bath and analyzed for its concentration of drug. If the drug exhibits a low migration into the polymer, that is the polymer rejects the passage of the drug, the polymer is useful for the present purpose. For example, if the preselected drug is progesterone and the film is formed polyethylene, the film would exhibit a permeability constant of $1.4 \times 10^{-5} cm^2/hr$, and if the film is polydimethyl siloxane, the film would exhibit a permeability constant of $8.0 \times 10^{-2} cm^2/hr$. Thus, for this preselected drug, polyethylene is used for manufacturing layer 27. Material demonstration a passage of zero to $1 \times 10^{-5}$ are operable for the intended purpose. The rate of rejection of a film can be determined by procedures described in *J. Pharm.* Vol. 52, pages 1145 to 1149, 1963; ibid. Vol. 53, pages 798 to 802; ibid. Vol. 55 pages 840 to 843, and 1224 to 1239, 1966; *Encyl. Polymer. Sci. Technol,* Vol. 5 and 9, pages 63 to 82 and 794 to 807, 1968, and the references acted therein.

The hydrophilic composition suitable for forming layer 28 are swellable, hydrophilic polymers. The presently preferred materials useful for forming layer 28 comprise hydrogels that exhibit the ability to swell and expand in the presence of water and retain a significant fraction of water within the hydrogel structure. The hydrogels can be noncross-linked, or they can be lightly crossed linked. The polymer hydrogels swell or expand to a very high degree in the presence of aqueous type fluids, usually exhibiting a 2 to 50 volume increase. This expansion against layers 27 and layer 26 results in the drug being delivered through exit passageway 23. Hydrophilic polymeric compositions useful for the present purpose include poly(hydroxyalkyl methacrylate); poly(N-vinyl-2-pyrrolidone); anionic hydrogels; cationic hydrogels; polyelectrolyte hydrogel complexes; poly(-vinyl alcohol) cross-linked with glyoxal, formaldehyde or glutaraldehyde; copolymers produced by forming a dispersion of finely divided copolymer of maleic anhydride with styrene, ethylene, propylene, butylene or isobutylene; polymeric N-vinyl lactams; acidic carboxypolymers available as Carbopol ® polymer; Cyanamer ® polyacrylamides cross-lined with indene-maleic anhydride; Good-Rite ® polyacrylic acid; Aqua-Keeps ® acrylate polymer; diester cross-linked polyglucan; polyethylene oxide; copolymers of N-vinyl lactam with N-vinyl pyrrolidone, N-vinyl caprolactam and N-vinyl piperidone; Water Lock ® starch-graft-poly(iodine acylate-co-acrylamide); and the like. The degree of expansion is calculated by subtracting the weight of the dry film from the weight of the aqueous swollen film divided by the weight of the dry film times 100.

The expression "exit means" 23 as used herein comprises means and methods suitable for dispensing the beneficial drug 26 through passageway 23 from dosage form 20. The means include at least one passageway or orifice that passes through wall 22 for communicating drug 26 with the exterior of dosage form 20. The expression "at least one passageway" includes aperture, orifice, bore, pore, porous element through which drug 26 can migrate, hollow fiber, capillary, and the like. The expression includes also a material that erodes or is leached from wall 22 in the fluid environment of use to produce at least one passageway of controlled releasing dimensions in the dosage form. The expression includes also a microporous member comprising preformed passageways or passageways formed in a fluid environment of use. Representative materials suitable for forming at least one passageway, or two passageways, include an erodible poly(glycolic) or poly(lactic) acid member in the wall, a gelatinous filament, poly(vinyl alcohol), leachable materials such as removable pore forming polysaccharides, salts or oxides, and the like. A passageway or a plurality of passageways can be formed by leaching a material such as sorbitol from the wall. The dosage form can be constructed with one or more passageways in a spaced apart relation on more than a single distant surface of a dosage form. Passageways and equipment for forming passageways are disclosed in U.S. Pat. Nos. 3,916,889; 4,063,064 and 4,088,864. Representative passageways formed by governed leaching to produce a pore of pre-controlled sizes are disclosed in U.S. Pat No. 4,200,098.

Wall 22 of osmotic dosage form 20 can be formed in one technique using the air suspension procedure. This procedure consists in suspending and tumbling the three compressed laminate in a current of air and wall forming composition until a wall is applied to the drug forming compartment. The air suspension procedure is well-suited for independently forming the wall. The air suspension procedure is described in U.S. Pat. No. 2,799,241; *J. Am. Pharm. Assoc.,* Vol. 48, pages 451 to 459, 1959; and ibid, Vol. 49, pages 82 to 84, 1960. Osmotic dosage forms can also be coated with a wall-forming composition in a Wurster ® air suspension coater, using methylene dichloride-methanol cosolvent, 80/20, v/v, using 2.5 to 4% solids. The Aeromatic ® air suspension coater using a methylene dichloride-methanol cosolvent, 87/13, v/v, also can be used for applying the wall. Other wall forming techniques such as pan coating can be used for providing the dosage form. In the pan coating system, wall forming compositions are deposited by successive spraying of the composition on the three layered compartment, accompanying by tumbling in a rotating pan. A pan coater is used to produce thicker walls. A larger volume of methanol can be used in a cosolvent to produce a thinner wall. Finally, the wall coated compartments are dried in a forced air oven at 50° C. for a week to free the dosage form of solvent. Generally, the walls formed by these techniques have a thickness of 2 to 20 mils with a presently preferred thickness of 4 to 10 mils.

Dosage form 20 of the invention is manufactured by standard manufacturing techniques. For example, in one manufacturer the beneficial drug and other ingredients comprising the first layer facing the exit means are blended and pressed into a solid layer. The layer possesses dimensions that correspond to the internal dimensions of the area the layer is to occupy in the dosage form and it also possesses dimensions corresponding to the second layer for forming a contacting arrangement therewith. The drug and other ingredients can be blended also with a solvent and mixed into a solid or semisolid formed by conventional methods such as ball-milling, calendering, stirring or rollmilling and then pressed into a preselected shape. Next, the middle is pressed against the first layer. The layer can be pressed as a film, or a layer of crystalline hydrophobic composition can be pressed against the first layer. Next, a layer of hydrogel is placed in contact with the hydrophobic middle layer. The layering of the drug layer, the middle layer and the hydrogel layer can be fabricated by conventional press-layering techniques. Finally, the three-layer compartment forming members are surrounded and coated with an outer wall. A passageway is laser drilled through the wall to contact the drug layer, with the dosage form optically oriented automatically by the laser equipment for forming the passageway on the preselected surface.

In another manufacture, the dosage form is manufactured by the wet granulation technique. In the wet granulation technique, the drug and the ingredients comprising the first layer are blended using an organic solvent, such as isopropyl alcohol-methylene dichloride 80/20 v/v (volume/volume) as the granulation fluid. Other granulating fluid such as denatured alcohol 100% can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 50° C. The dry granules are sized then with a 20 mesh screen. Next, magnesium stearate is passed through an 80 mesh screen and added to the dry screen granule blend. The granulation is put into milling jars and mixed on a jar mill for 10 to 15 minutes. The composition is pressed into layers, for example in a Manesty ® press layer press. The middle and third layers are pressed in a similar manner.

Another manufacturing process that can be used for providing the compartment-forming composition comprises blending the powdered ingredients in a fluid bed granulator. After the powdered ingredients are dry blended in the granulator, a granulating fluid, for example poly(vinyl-pyrrolidone) in water, is sprayed onto the powders. The coated powders are then dried in a granulator. This process granulates all the ingredients present therein while adding the granulating fluid. After the granules are dried, a lubricant such as stearic acid or magnesium stearate is added to the granulator. The granules are pressed then in the manner described above.

A novel dosage form provided by the invention is manufactured as described hereinafter. First, 75.5% (based on a 300 g batch) of mannitol, granular is put through a 40 mesh screen and sieved through a 60 mesh screen (all the mannitol that went through the 60 mesh screen is used for preparing the dosage form). Next, chlorpheniramine maleate 14%, microcrystalline cellulose 5%, and polyvinyl pyrrolidone independently are screened through a 40 mesh screen, and the screened ingredients mixed in a blender with the mannitol for about 20 minutes to produce a homogeneous blend. Next, 0.5% silicon dioxide is screened through the 80 mesh screen, and then 1% magnesium stearate is screen through the 80 mesh screen. The screened silicon dioxide and the screened magnesium stearate are added to the blend comprising the mannitol, chlorpheniramine, microcrystalline cellulose and polyvinyl pyrrolidone, and blended for 5 minutes.

Next, 93% phenylene oxide having a molecular weight of about 5,000,000; 5% hydroxypropylmethyl cellulose; and 1% ferric oxide are wet granulated using ethyl alcohol as the granulating fluid. The wet granulation is screened through a 16 mesh screen and dried on trays at 50° C. in an oven overnight. The dried granulation is screened through a 16 mesh screen. Then, 1% magnesium stearate is screened through a 80 mesh screen and added to the dried granulation. Finally, all of the ingredients are blended for 5 minutes to yield a homogeneous blend.

A dosage form comprising a first drug layer, a middle hydrophobic layer and a third hydrophilic layer is prepared in a Carver ® press using a ¼ inch, standard concave die. First, 86 mg of the composition comprising the drug chlorpheniramine is placed in the die and pinched to compress the granulation. Next, a middle-forming layer comprising 20 mg of flakes of caranuba wax is placed on tap of the drug layer and compressed to form a continuous middle layer. Then, the third-forming layer comprising phenylene oxide hydrophilic polymer is placed on top of the middle layer and compressed with 2.5 tons of force.

Figure 3:
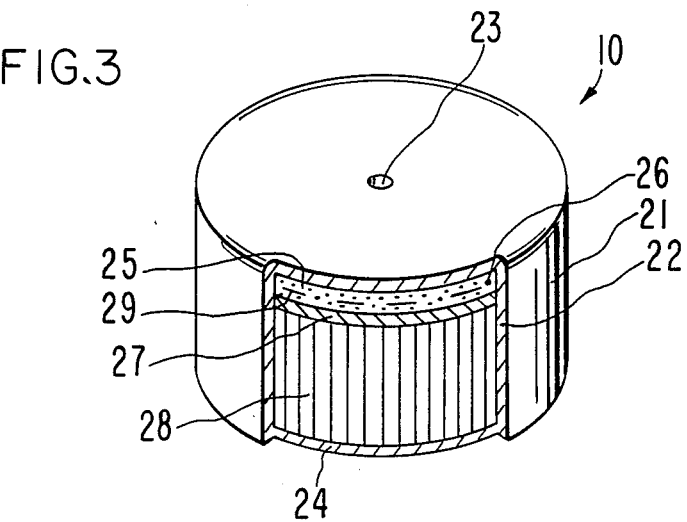

The three-layered laminate is surrounded with a wall in an Aeromatic ® Coater. The wall-forming composition comprised 51 g of cellulose acetate having an acetyl content of 43.5%, 9 g of hydroxypropyl cellulose, and a cosolvent comprising 1,170 ml of methylene chloride and 490 ml of methanol. During the wall-forming process, 960 ml of wall-forming solution are used to apply a 12.3 mg wall on each three-layered dosage form. The dosage forms are dried in an oven overnight at 50° C. to yield a final dry wall of 10.4 mg per dosage form. A single 15 mil, (0.325 mm) passageway is drilled through the wall connecting the exterior of the dosage form with the first layer. The first layer is selected by visual examination. In an automatic laser drilling technique, the drug layer is selected by the photo examination apparatus of the laser. The dosage form delivers 98.6% of chlorpheniramine maleate in 24 hrs as determined by cumulative amount released assay. The dosage form at the end of the delivery period is illustrated in FIG. 3, wherein the first layer is substantially delivered from the dosage form.

The above procedure is repeated with all the conditions as set forth, except that the middle layer in this example comprises a microcrystalline polyolefin, polyethylene. The microcrystalline polyethylene had an average particle size of 3 microns.

The dosage form provided by the invention release the beneficial drug throughout the gastrointestinal tract, including in the acidic environment of the stomach and in the alkaline environment of the intestine. It will be appreciated the present invention contributes to the delivery art an unobvious dosage form that possesses practical utility. While the invention has been described and pointed out in details with reference to operative embodiments thereof, it will be understood that those skilled in the art will appreciate the various changes, modifications, substitution and omissions can be made without departing from the spirit of the invention. It is intended therefore, that the invention embrace those equivalents within the scope of the claims which follow.

We claim:

1. A dosage form for delivering a beneficial agent to the fluid environment of use, comprising:
   (a) a wall in at least a part a semipermeable composition permeable to the passage of an exterior fluid and substantially impermeable to the passage of a beneficial agent, which wall surrounds and forms:
   (b) a compartment;
   (c) a first layer comprising a beneficial agent in the compartment, which layer forms in situ a dispensable aqueous formulation comprising the beneficial agent with aqueous fluid that enters the compartment;
   (d) a third layer comprising hydrogel means for expanding and occupying space in the presence of fluid in the compartment;
   (e) a second layer pressed laminated into laminar arrangement between the first and third layer in the compartment, said second layer comprising a thickness of 1 to 7 mm and a permeability constant not more than about $1.0 \times 10^{-5} cm^2/hr$ and being a separate and distinct layer comprising a different composition than the first and third layers, which second layer comprises a non-expandable hydrophobic composition that is a means for substantially preventing the migration of the beneficial agent from the first layer comprising the dispensable aqueous formulation into the third layer; and,
   (f) means in the wall connecting the exterior of the dosage form with the compartment.

2. The dosage form for delivering the beneficial agent to a fluid environment of use according to claim 1, wherein the means connecting the exterior of the dosage form with the internal compartment comprises at least one passageway.

3. The dosage form for delivering the beneficial agent to a fluid environment of use according to claim 1, wherein the beneficial agent is chlorpheniramine.

4. The dosage form for delivering the beneficial agent to a fluid environment of use according to claim 1, wherein the means for connecting the exterior of the dosage form with the interior compartment is a microporous member.

5. The dosage form for delivering the beneficial agent to a fluid environment of use according to claim 1, wherein the means in the wall connecting the exterior of the dosage form with the compartment is a passageway pore formed by leaching a material from the wall.

* * * * *